United States Patent [19]
Cody et al.

[11] Patent Number: 5,919,481
[45] Date of Patent: Jul. 6, 1999

[54] FILL MATERIAL FOR SOFT GELATIN PHARMACEUTICAL DOSAGE FORM

[75] Inventors: Sharon L. Cody, Erie; Brid T. Devlin, Conshohocken; John Dubek, Philadelphia; Michael R. Hoy, Sellersville, all of Pa.

[73] Assignee: NcNeil-PPC, Inc., Skillman, N.J.

[21] Appl. No.: 08/671,991

[22] Filed: Jun. 28, 1996

[51] Int. Cl.$^6$ .................................................... A61K 9/48
[52] U.S. Cl. ......................... 424/452; 424/454; 424/455; 424/456; 514/772.3; 514/781
[58] Field of Search ................................. 424/451, 452, 424/455, 456, 454, 453

[56] References Cited

U.S. PATENT DOCUMENTS

| | | | |
|---|---|---|---|
| 4,028,024 | 6/1977 | Moreland | 425/133.1 |
| 4,486,412 | 12/1984 | Shah et al. | 424/156 |
| 4,708,834 | 11/1987 | Cohen et al. | 264/4.3 |
| 4,734,284 | 3/1988 | Terada et al. | 424/455 |
| 4,935,243 | 6/1990 | Borkan et al. | 424/452 |
| 5,071,643 | 12/1991 | Yu et al. | 514/570 |
| 5,085,033 | 2/1992 | Graham | 53/436 |
| 5,431,916 | 7/1995 | White | 424/451 |

FOREIGN PATENT DOCUMENTS

| | | |
|---|---|---|
| 0 571 217 A2 | 11/1993 | European Pat. Off. . |
| 0 587 220 A1 | 3/1994 | European Pat. Off. . |
| 298351 A5 | 2/1992 | Germany . |
| 63-222121 | 9/1988 | Japan . |
| WO 91/07950 | 6/1991 | WIPO . |
| WO 95 01166 | 1/1995 | WIPO . |
| WO 95 23591 | 9/1995 | WIPO . |

OTHER PUBLICATIONS

Derwent Abstract of JP 63–222121 (WPI Acc No.: 88–303260/43) Sep. 1988.
Database WPI, Section Ch, Week 9240, Derwent Pub. Ltd., London, G.B.; Class A, p. 96, AN 92–328089, Abstract of JP 04 235 916 A (Aug. 25, 1992).
Remington's Pharmaceutical Sciences, 18th Ed., Chapter 83, pp. 1539–1540 (1990).

*Primary Examiner*—Thurman K. Page
*Assistant Examiner*—James M. Spear
*Attorney, Agent, or Firm*—Bernard F. Plantz

[57] ABSTRACT

The present invention relates to a substantially translucent, semi-solid fill material for a soft gelatin capsule containing a therapeutically effective amount of a pharmaceutical dissolved or suspended in the semi-solid. The semi-solid is sufficiently viscous so that it cannot be readily expelled at room temperature from the capsule with a syringe.

29 Claims, No Drawings

FILL MATERIAL FOR SOFT GELATIN PHARMACEUTICAL DOSAGE FORM

FIELD OF THE INVENTION

The present invention relates to a soft gelatin capsule filled with a semi-solid containing a therapeutically effective amount of a pharmaceutical dissolved or suspended in the semi-solid and, more particularly, to a semi-solid fill material that has a substantially translucent appearance.

This invention is also related to commonly assigned U.S. patent application Ser. Nos. 08/366,945, filed Dec. 29, 1994 abandoned, entitled "Soft Gelatin Pharmaceutical Dosage Form"; 08/366,271, filed Dec. 29, 1994 U.S. Pat. No. 5,660,859, entitled "Gelling Agent for Polyethylene Glycol"; Ser. No. 08/671,988, filed Jun. 28, 1996, entitled "Fill Material for Soft Gelatin Pharmaceutical Dosage Form containing an Antiflatulent"; and Ser. No. 08/671,979, filed Jun. 28, 1996, entitled "Multiphase Soft Gelatin Dosage Form", all of which are hereby incorporated by reference.

BACKGROUND OF THE INVENTION

In recent years soft gelatin or soft elastic gelatin capsules have become a popular dosage form for the oral delivery of therapeutic agents, especially over-the-counter pharmaceuticals. These capsules are typically filled with a liquid containing the active ingredient. Because of their soft, elastic character, some patients view these capsules as easier to swallow than conventional tablets or hard gelatin capsules. Since the dosage form is generally swallowed, it is not necessary to flavor or otherwise mask the often unpleasant taste of the pharmaceutical. Soft gelatin capsules are also preferred to bulk liquids because they are easier to transport and they avoid the need for the patient to measure a prescribed amount of the liquid before dosing.

The fill material used in a soft gelatin capsule generally contains a pharmaceutical dissolved or dispersed in a carrier that is compatible with the capsule wall. In addition to liquids, U.S. Pat. No. 4,935,243 to L. Borkan et al. suggests that the fill material may take the form of a semi-solid, solid, or gel. Conventional tablets or pellets containing an active ingredient are examples of solid fill materials that may be encapsulated within a soft gelatin capsule.

Semi-solid (dispersion) fill material are discussed in U.S. Pat. No. 4,486,412 to D. Shah et al. A fill material containing an orally-administered antacid salt that is dispersed in a water-free, liquid carrier containing a major proportion of one or more polyalkylene glycols and a minor proportion of a $C_2$-$C_5$ polyol, such as propylene glycol or glycerin. The carrier forms a stable dispersion of the antacid salt and coats the antacid particles, thereby rendering them non-reactive with the soft gelatin capsule wall.

U.S. Pat. No. 4,708,834 to Cohen et al. suggests a controlled release pharmaceutical dosage form comprising a soft gelatin capsule that encloses a water-soluble or dispersible gelled polymer matrix. The fill material comprises an aqueous solution or dispersion of a polysaccharide gum, the pharmaceutical active and, optionally, an alcohol. The liquid fill is introduced into a soft gelatin capsule that contains a cationic gelling agent, which gels the liquid fill after it has been incorporated into the capsule shell. The alcohol used in the fill includes liquid polyethylene glycols, lower alkanols, $C_2$-$C_4$ polyols and mixtures thereof.

U.S. Pat. No. 5,071,643 to M. Yu et al. also discusses the use of polyethylene glycols (PEG) as a fill material in soft gelatin dosage forms. PEGs having an average molecular weight between 400–600 are preferred for liquid fills, between 800–10,000 for semi-solid fills and between 10,000–100,000 for solid fills.

*Remington's Pharmaceutical Sciences,* 18th ed, Chapter 83, pp. 1539–40 (1990), reports that gelling agents used to make gels for pharmaceutical and cosmetic products, include sodium alginate and triethanolamine.

PCT Publication No. WO 91/07950 describes a soft or two-piece hard gelatin capsule shell containing benzodiazepine dissolved or suspended in a gel. The gel contains by weight at least 63% of polyethylene glycol 600, at least 4% of polyethylene glycol 4000 or 6000, and at least 21% of polyethylene glycol 600–4000. This gel fill cannot be readily expelled with a syringe at ambient temperature and therefore avoids the reported abuse of liquid filled capsules by intravenous drug abusers. As reported in Example 1 of the present application, gels containing this blend of polyethylene glycols have an opaque appearance.

A need exists for a substantially translucent, semi-solid fill material suitable for use in the production of soft gelatin capsules. The fill material should also be sufficiently viscous so as to prevent it from being expelled from the capsule shell with a syringe.

SUMMARY OF THE INVENTION

The present invention provides a fill material for a soft gelatin capsule comprising a polyalkylene glycol having an average molecular weight of about 600 or less, a thickening agent in an amount effective to thicken the glycol to form a semi-solid, and, optionally, water. A therapeutically effective amount of a pharmaceutical is dissolved or suspended in the semi-solid, and the semi-solid gel has a turbidity of less than about 1300 NTU (Nephelometric Turbidity Unit).

The semi-solid of the present invention has a substantially translucent appearance, and when used to fill a soft gelatin capsule, which is also translucent, the resulting dosage form has an elegant, substantially translucent or clear appearance.

In a further embodiment of the present invention, the semi-solid is sufficiently viscous so that it cannot be readily expelled at room temperature from the capsule with a syringe, preferably having an 16 gauge or smaller needle.

DETAILED DESCRIPTION OF THE PREFERRED EMBODIMENTS

The present invention relates to a substantially translucent semi-solid for filling a soft gelatin capsule pharmaceutical dosage form. The semi-solid may also be used to fill a two-piece hard gelatin capsule. The viscosity of the semi-solid is also controlled so that the fill cannot be readily removed from the capsule with a syringe at room temperature. This feature helps to protect against possible intravenous abuse of the drug as well as product tampering.

As used in the present invention, a semi-solid is a system of at least two constituents consisting of a condensed mass enclosing and interpenetrated by a liquid. The semi-solid fill material is sufficiently viscous so that an appreciable amount, less than about 1, preferably less than about 0.5, gram, cannot be expelled at room temperature with a syringe having a 16 gauge or smaller needle. The semi-solid preferably has a viscosity at 25° C. of at least about 30,000, most preferably at least about 200,000, centipoise (cP). The viscosity of the semi-solid is generally less than about 500,000 cP.

The semi-solid of the present invention contains a liquid polyalkylene glycol having an average molecular weight of about 600 or less. The polyalkylene glycol serves as a solvent for the pharmaceutical. A suitable polyalkylene glycol is polyethylene glycol. The polyethylene glycols preferably have an average molecular weight of about 200 to about 600, and most preferably about 300 to about 400. The semi-solid generally comprises by weight about 35 to about 99, preferably about 85 to 99, percent solvent. Unless otherwise stated, the percentages recited herein are by weight of the total weight of the semi-solid fill material, i.e., both the semi-solid and active ingredient.

The semi-solid is formed by thickening the solvent with cellulose ethers. A suitable cellulose ether is hydroxypropyl cellulose. Preferably the thickening agent is hydroxypropyl cellulose, NF having a molecular weight of about 80,000 to about 1,150,000. Hydroxypropyl cellulose, NF is commercially available from Aqualon, Inc. under the tradename KLUCEL®, and the preferred grades are KLUCEL GF, MF and HF having a molecular weight range of about 370,000 to about 1,150,000. Lower molecular weight hydroxypropyl cellulose, including KLUCEL EF, LF and JF, having a range of about 80,000 to about 140,000 may also be used, but generally at higher concentrations than the higher molecular weight grades.

In a preferred embodiment, the thickening agent is employed in an amount effective to form a semi-solid that is substantially translucent and is sufficiently viscous so that it cannot be expelled at room temperature with a syringe having an 16 gauge or smaller needle. Generally the semi-solid contains by weight from about 0.10 to about 10, preferably about 0.25 to about 3.5, percent of one or more of the cellulose ethers.

In addition to the liquid polyalkylene glycol, the semi-solid may contain solubilizing agents to enhance the solubility or dispersibility of the active ingredient in the semi-solid. Suitable agents include propylene glycol, glycerin, ethanol, N-methyl-2-pyrrolidone, dimethyl isosorbide, povidone (PVP), poloxamer, other pharmaceutically acceptable surfactants and mixtures thereof. A preferred poloxamer (poly(oxyethylene)-poly(oxypropylene) copolymer) is Poloxamer 124, available from BASF under the tradename PLURONIC L 44. The semi-solid generally comprises 0 to about 8, preferably 0 to about 6, percent of the solubilizing agent. In addition, the semi-solid may contain 0 to about 10 percent water.

If acetaminophen, famotidine, ranitidine, cimetidine or other readily oxidizable substance is used as the active ingredient, it may desirable to include an antioxidant to eliminate degradation or discoloration, such as "pinking" of acetaminophen.

The pharmaceutical active(s) is present in the dosage form in a therapeutically effective amount, which is an amount that produces the desired therapeutic response upon oral administration, and can be readily determined by one skilled in the art. In determining such amounts, the particular compound being administered, the bioavailability characteristics of the compound, the dose regimen, the age and weight of the patient, and other factors must be considered. Pharmaceuticals suitable for use in the invention include acetaminophen, famotidine, chlorpheniramine, pseudoephedrine, dextromethorphan, diphenhydramine, brompheniramine, clemastine, phenylpropanolamine, terfenadine, astemizole, loratadine, loperamide, loperamide-N-oxide, ranitidine, cimetidine, tramadol, cisapride, acetylsalicylic acid, doxylamine succinate, pharmaceutically acceptable salts thereof and mixtures thereof. Generally, the pharmaceutical comprises about 0.1 to about 40, preferably about 0.2 to about 30, percent by weight of the total semi-solid composition.

Various other pharmaceutically acceptable excipients may be included in the semi-solid fill material, such as preservatives, e.g., methyl- or propylparaben, coloring agents, flavoring agents, lubricants, flow-enhancers, antioxidants, surfactants, plasticizers, filling aids and other compounds, agents and components which produce an appealing final product.

In a preferred embodiment, a fill for a soft gelatin capsule containing about 180 mg/mL acetaminophen, comprises by weight about 10 to about 40 percent acetaminophen, about 40 to about 90 percent polyethylene glycol having an average molecular weight of about 400 (PEG 400), 0 to about 8 percent water, from 0 to about 8 percent propylene glycol, and from about 2 to about 8 percent hydroxypropyl cellulose.

In a still further preferred embodiment, a fill for a soft gelatin capsule containing from 10–40 mg/mL famotidine, comprises by weight about 0.5 to about 4 percent famotidine, from about 60 to about 99 percent PEG 400, from 0 to about 8 percent water, from 0 to about 8 percent, propylene glycol, and from about 2 to about 8 percent hydroxypropyl cellulose.

In a still further preferred embodiment a fill for a soft gelatin capsule containing 17 mg/mL loperamide HCl, comprises by weight about 1 to about 3 percent loperamide HCl, from about 92 to about 99 percent PEG 400, from 0 to about 8 percent water, from 0 to about 8 percent propylene glycol, and from about 0.5 to about 3 percent hydroxypropyl cellulose.

The fill material of the present invention may be used in commercially available soft gelatin capsules, such as those commercially available from R. P. Scherer or Banner Pharmacaps. Various sizes, shapes, and colors can be used to accommodate different levels of active ingredients. The walls of the capsules have a substantially translucent or clear appearance. When the fill material of the present invention is introduced into the capsule and forms a semi-solid, the resulting dosage form has an elegant, translucent or clear appearance. The fill material generally has turbidity less than about 1300, preferably less than about 200, NTU.

The fill material is heated before it is loaded into the capsule because it is highly viscous at temperatures below 40° C. Air-filled soft gelatin capsules can be hand filled with a syringe. The hot liquid fill is loaded into a syringe. The needle on the syringe is used to puncture one end of the soft gelatin capsule so that the appropriate amount of fill material may be injected by hand. The capsule with fill material is allowed to cool.

The fill material may also be introduced into the soft gelatin capsule using encapsulation equipment known in the art, such as that described in U.S. Pat. No. 4,028,024 to Moreland, which is hereby incorporated by reference. As previously described with the hand-filling technique, the fill must be maintained at about 40° C. during the filling operation so that it readily flows into the capsule. Therefore, the fill can be stored in a jacketed vessel and transported through a thermostatically controlled feeding tube to the encapsulation equipment.

Specific embodiments of the present invention are illustrated by way of the following examples. This invention is not confined to the specific limitations set forth in these examples, but rather to the scope of the appended claims. Unless otherwise stated, the percentages and ratios given below are by weight of the total composition.

The turbidity of the fill materials described in the following examples was measured using a Hach Ratio/XR Turbidimeter. The United States Pharmacopeia defines turbidance as the light-scattering effect of suspended particles and turbidity as the measure of the decrease in the incident beam intensity per unit length of a given suspension. This instrument measures turbidity within a range of 0.00 to 2000 NTU. As a point of reference, the turbidity of water is zero. Samples of the fill materials, approximately 8 mL, were transferred to Fisher Brand 13×100 mm culture tubes immediately after manufacture. The fill material samples were stored at ambient room temperature since they were made several days in advance. The outer surface of each of the sample culture tubes was treated with silicone oil just prior to measuring the turbidity. The turbidity of the samples was measured at ambient room temperature. The turbidity of two sample tubes of each fill material was measured and the average of the results is reported.

Viscosity was measured in the following examples using a Rheometrics Fluids Spectrometer 8400 at 25° C. Using a 25 mm parallel plate and a constant strain of 10%, frequency sweeps were performed. Viscosity was recorded at a frequency of 1.0 radian per second.

Dissolution testing was performed in the following examples using USP type I baskets set at 100 rpm. and an acetate buffer (pH 4.7) with pepsin as the medium. Volume was 500 mL, the USP limits are NMT 80% in 30 minutes. An amount of the formulation equivalent to a 4.0 mg. dose of loperamide HCl was tested on a soft gelatine capsule cut in half.

Syringeability testing was performed in the following examples to measure the ability to syringe each formulation within a controlled time period. This test was used as a gauge of tamper resistance. 10 cc syringes were used with 16 gauge needles, 1.5 inches in length. The syringe was placed in the formulation, the plunger was pulled up and held for 10 seconds. The weight of the fill material pulled into the syringe was recorded.

EXAMPLE 1

This Example provides a comparison of the PEG blends similar to those described in PCT Publication WO 91/07950. The following blends were prepared:

|  | Amount (% w/w) | |
| --- | --- | --- |
| Component | Sample A | Sample B |
| PEG 600 | 64.40 | 64.40 |
| PEG 1450 | 26.20 | 26.20 |
| PEG 3500 | — | 4.20 |
| PEG 8000 | 4.20 | — |
| Glycerol | 5.20 | 5.20 |

The samples were prepared as follows:

1) Weigh PEGs and glycerol.
2) Place mixture on preheated hot plate set to highest setting. Mix with heat (approximately 75° C.) until a clear solution is obtained.
3) Remove mixture from heat and mixing. Sonicate with heat temp set=69° C. Upon cooling to RT to form a gel, both Samples had an opaque white appearance with a turbidity exceeding 2000 NTU.

EXAMPLE 2

This Example discloses a fill material of the present invention containing about 180 mg/mL of acetaminophen. The fill contains:

| Component | Amount (% w/w) |
| --- | --- |
| Acetaminophen | 20.0 |
| PEG-400 (400 MW) | 75.7 |
| Hydroxypropyl Cellulose (KLUCEL GF;300,000 MW) | 4.3 |

The sample is prepared as follows:

1) PEG-400 is heated to 110–120° C. and the acetaminophen is slowly added while stirring.
2) After the acetaminophen goes into solution, the hydroxypropyl cellulose is added while stirring.
3) After the resulting mixture appears to be a clear solution, it is allowed to cool to room temperature.

EXAMPLE 3

This Example discloses a fill material of the present invention containing 10 mg/mL of famotidine. The fill material contained:

| Component | Amount (% w/w) |
| --- | --- |
| Famotidine | 1.6 |
| PEG 400 (400 MW) | 91.3 |
| Hydroxypropyl Cellulose (KLUCEL GF;300,000 MW) | 7.1 |

The sample was prepared as follows:

1) PEG-400 was heated to 110–120° C. and the hydroxypropyl cellulose was slowly added while stirring.
2) After the hydroxypropyl cellulose went into solution, the formulation was cooled to about 70° C.
3) The famotidine was added while stirring.
4) After the resulting mixture appeared to be a clear solution, it was allowed to cool to room temperature to give a clear, semi-solid.

The turbidity of the resulting sample was 14.6 NTU.

EXAMPLE 4

This Example discloses a semi-solid fill material of the present invention containing 17 mg/mL of loperamide HCl. The fill materials contained:

| Component | Amount (% w/w) |
| --- | --- |
| Hydroxypropyl Cellulose (KLUCEL HF; 1,150,000 MW) | 1.5 |
| PEG 400 (400 MW) | 89 |
| Loperamide HCl | 1.5 |
| Poloxamer (PLURONIC L-44) | 8 |

The sample was prepared as follows:

1) PEG 400 and poloxamer were heated to 100° C. and the hydroxypropyl cellulose was slowly added while stirring at high speed on a hot plate.
2) After the hydroxypropyl cellulose went into solution, the formulation was cooled to about 70° C.
3) The hydroxypropyl cellulose was slowly added while stirring.

4) After the resulting mixture appeared to be a clear solution, it was allowed to cool to room temperature to give a clear, semi-solid.

The resulting formulations were allowed to cool to room temperature to give a clear, semi-solid.

EXAMPLE 5

This Example discloses semi-solid fill materials containing 17 mg/mL of loperamide HCl. The fill materials contained:

| Component | Amount (% w/w): A | B |
|---|---|---|
| Hydroxypropyl Cellulose (KLUCEL MF; 850,000 MW) | 3.0 | 3.0 |
| Propylene Glycol | — | 6.0 |
| PEG 400 | 95.5 | 89.5 |
| Loperamide HCl | 1.5 | 1.5 |

The samples were prepared as follows:
1) Weigh PEG 400, propylene glycol and hydroxypropyl cellulose into beaker.
2) Mix at high speed on hot plate, set to approx. 120° C., until polymer is completely dissolved.
3) Reduce heat to approx. 70° C. and add loperamide HCl, mix until dissolved.

The resulting formulations were allowed to cool to a clear, semi-solid.

EXAMPLE 6

This Example discloses a semi-solid fill material containing 17 mg/mL loperamide HCl. The fill material contained:

| Component | Amount (% w/w): |
|---|---|
| Hydroxypropyl Cellulose (KLUCEL HF; 1,150,000 MW) | 1.5 |
| Propylene Glycol | 5.5 |
| PEG 400 | 91.5 |
| Loperamide HCl | 1.5 |

The sample was prepared as follows:
1) Weigh PEG 400, propylene glycol and hydroxypropyl cellulose into beaker.
2) Mix at high speed on hot plate, set to approx. 120° C., until polymer is completely dissolved.
3) Reduce heat to approx. 70° C. and add loperamide HCl, mix until dissolved.

The resulting formulation was allowed to cool to room temperature to give a clear semi-solid.

EXAMPLE 7

This Example discloses a semi-solid fill material containing 17 mg/mL of loperamide HCl.

| Component | Amount (% w/w): |
|---|---|
| Hydroxypropyl Cellulose (KLUCEL MF; 850,000 MW) | 2.7 |
| Propylene Glycol | 5.5 |
| PEG 400 | 90.3 |
| Loperamide HCl | 1.5 |

The sample was prepared as follows:
1) Weigh PEG 400, propylene glycol and hydroxypropyl cellulose into beaker.
2) Mix at high speed on hot plate, set to approx. 120° C., until polymer is completely dissolved.
3) Reduce heat to approx. 70° C. and add loperamide HCl, mix until dissolved.

The resulting formulation was allowed to cool to room temperature to give a clear semi-solid.

The following summarizes the results of the sample testing for Examples 1 and 3–7:

| Example | Syringeability (g) | Clarity (NTU) | Viscosity (cPs) |
|---|---|---|---|
| 1A | — | >2000 | — |
| 1B | — | >2000 | — |
| 3 | — | 14.6 | — |
| 4 | 0.06 | — | 69,810 |
| 5A | 0.08 | 34 | 18,200 |
| 5B | 0.06 | 21 | 87,870 |
| 6 | 0.32 | 5.5 | 78,070 |
| 7 | 0.23 | 10.2 | 156,900 |
| Robitussin ® Liqui-Gels ® | 1.6 | — | — |
| Drixoral ® Cough Liqui-Gels ® | 3.2 | — | — |
| Water | 11.5 | — | — |

EXAMPLE 8

This Example discloses a soft gelatin capsule filled with a semi-solid fill material containing 17 mg/mL of loperamide HCl. The following sample was prepared:

| Component | Amount (% w/w): |
|---|---|
| Hydroxypropyl Cellulose (KLUCEL MF; 850,000 MW) | 2.7 |
| Propylene Glycol | 5.5 |
| PEG 400 | 90.3 |
| Loperamide HCl | 1.5 |

The sample was prepared as follows:
1) Weigh PEG 400, propylene glycol and hydroxypropyl cellulose into beaker.
2) Mix at high speed on hot plate, set to approx. 120° C., until polymer was completely dissolved.
3) Reduce heat to approx. 70° C. and add loperamide HCl, mix until dissolved.

The resulting formulation was allowed to cool to room temperature to give a clear semi-solid having a turbidity of approximately 7.0 NTU, a dissolution of approximately 95% loperamide HCl in 30 minutes and a syringeability of approximately 0.40 gram.

The semi-solid was warmed so that it would flow and then filled into hydrophobic and hydrophilic soft gelatin capsules as follows:
1) A 10 cc syringe barrel was filled with the loperamide HCl formulation, without the needle.

2) A 16 gauge needle was attached and was placed inside a pre-weighed air-filled soft gelatin capsule.

3) A 2 mg dosage of loperamide HCl was carefully syringed into the air-filled capsule.

4) The top of the air-filled capsule was sealed with a hot iron.

The resulting soft gelatin capsules had a substantially translucent appearance.

Various modifications can be made to the above-described embodiments without departing from the spirit and scope of the present invention.

What is claimed is:

1. A pharmaceutical composition, comprising:
   a semi-solid comprising a polyalkylene glycol having an average molecular weight of about 600 or less and a cellulose ether in an amount effective to thicken the polyalkylene glycol;
   a therapeutically effective amount of a pharmaceutical selected from the group consisting of acetaminophen, famotidine, chlorpheniramine, pseudoephedrine, dextromethorphan, diphenhydramine, brompheniramine, clemastine, phenylpropanolamine, terfenadine, astemizole, loratadine, loperamide, loperamide-N-oxide, ranitidine, cimetidine, tramadol, cisapride, acetylsalicylic acid, doxylamine succinate, pharmaceutically acceptable salts thereof, and mixtures thereof dissolved or suspended in said semi-solid; and
   said composition having a turbidity less than about 1300 NTU.

2. The composition of claim 1 wherein the polyalkylene glycol is polyethylene glycol.

3. The composition of claim 1 wherein the turbidity is less than about 200 NTU.

4. The composition of claim 1 further comprising propylene glycol.

5. The composition of claim 1, comprising by weight:
   about 35 to about 99 percent of the polyalkylene glycol;
   0 to about 10 percent propylene glycol;
   0 to about 10 percent of water; and
   about 0.1 to about 10 percent of the cellulose ether.

6. The composition of claim 5 comprising polyethylene glycol having an average molecular weight of about 200 to about 600.

7. The composition of claim 1 wherein the cellulose ether is hydroxypropyl cellulose.

8. The composition of claim 7 wherein the cellulose ether is hydroxypropyl cellulose having a molecular weight of about 80,000 to about 1,150,000.

9. A pharmaceutical dosage form, comprising:
   a gelatin capsule shell filled with a semi-solid containing a therapeutically effective amount of a pharmaceutical selected from the group consisting of acetaminophen, famotidine, chlorpheniramine, pseudoephedrine, dextromethorphan, diphenhydramine, brompheniramine, clemastine, phenylpropanolamine, terfenadine, astemizole, loratadine, loperamide, loperamide-N-oxide, ranitidine, cimetidine, tramadol, cisapride, acetylsalicylic acid, doxylamine succinate, pharmaceutically acceptable salts thereof, and mixtures thereof dissolved or suspended in said semi-solid; and
   said semi-solid containing the pharmaceutical having a turbidity less than about 1300 NTU.

10. The composition of claim 1 wherein said semi-solid comprises polyethylene glycol having an average molecular weight of about 300 to about 400 and hydroxypropyl cellulose.

11. The composition of claim 10, comprising by weight:
    about 85 to about 99 percent of polyethylene glycol having an average molecular weight of about 300 to about 400;
    0 to about 8 percent propylene glycol; and
    about 0.25 to about 3.5 percent of a hydroxypropyl cellulose having an average molecular weight of about 300,000 to about 1,200,000.

12. The composition of claim 1 having a viscosity of at least 30,000 centipoise.

13. The composition of claim 12, comprising by weight:
    about 1 to about 3 percent loperamide HCl;
    about 92 to about 99 percent polyethylene glycol having an average molecular weight of about 400;
    0 to about 8 percent water;
    0 to about 8 percent propylene glycol; and
    about 0.5 to about 3 percent hydroxypropyl cellulose.

14. The composition of claim 1 comprising by weight about 89 percent polyethylene glycol having an average molecular weight of about 400, about 8 percent polyoxyethylene)-poly(oxypropylene) copolymer, about 1.5 percent hydroxypropyl cellulose and about 1.5 percent loperamide HCl.

15. The dosage form of claim 9, wherein the shell is a soft gelatin capsule.

16. The dosage form of claim 9 wherein the turbidity of the semi-solid is less than about 200 NTU.

17. The dosage form of claim 9 wherein said semi-solid comprises a solvent and a thickening agent.

18. The dosage form of claim 17 wherein the solvent is polyalkylene glycol having an average molecular weight of about 600 or less, and the thickening agent is a cellulose ether in an amount effective to thicken said solvent.

19. The dosage form of claim 18 further comprises propylene glycol.

20. The dosage form of claim 18 wherein the polyalkylene glycol is polyethylene glycol.

21. The dosage form of claim 18, comprising by weight:
    about 35 to about 99 percent of polyalkylene glycol;
    0 to about 10 percent propylene glycol;
    0 to about 10 percent of water; and
    about 0.10 to about 10 percent of the cellulose ether.

22. The dosage form of claim 21 comprising polyethylene glycol having an average molecular weight of about 200 to about 600.

23. The dosage form of claim 18 wherein the cellulose ether is hydroxypropyl cellulose.

24. The dosage form of claim 23 wherein the cellulose ether is hydroxypropyl cellulose having a molecular weight of about 80,000 to about 1,150,000.

25. The dosage form of claim 17, comprising by weight about 89 percent polyethylene glycol having an average molecular weight of about 400, about 8 percent polyoxyethylene)-poly(oxypropylene) copolymer, about 1.5 percent hydroxypropyl cellulose and about 1.5 percent loperamide HCl.

26. The dosage form of claim 18 wherein said semi-solid comprises polyethylene glycol having an average molecular weight of about 300 to about 400 and hydroxypropyl cellulose.

27. The dosage form of claim 26, comprising by weight:
    about 85 to about 99 percent of polyethylene glycol, propylene glycol or mixtures thereof having an average molecular weight of about 300 to about 400;
    about 0 to about 6 percent propylene glycol; and about 0.25 to about 3.5 percent of hydroxypropyl cellulose having an average molecular weight of about 300,000 to about 1,200,000.

28. The dosage form of claim 9 having a viscosity of at least 30,000 centipoise.

29. The dosage form of claim 28, comprising by weight:

about 1 to about 3 percent loperamide HCl;

about 92 to about 99 percent polyethylene glycol having an average molecular weight of about 400;

0 to about 8 percent water;

0 to about 8 percent propylene glycol; and about 0.5 to about 3 percent hydroxypropyl cellulose.

* * * * *